United States Patent
Bastioli et al.

(10) Patent No.: US 8,629,290 B2
(45) Date of Patent: Jan. 14, 2014

(54) TRIGYCERIDES CONTAINING CERTAIN SATURATED CARBOXYLIC ACIDS

(75) Inventors: Catia Bastioli, Novara (IT); Giampietro Borsotti, Novara (IT); Alessandra Merlin, Galliate (IT); Tiziana Milizia, Novara (IT)

(73) Assignee: Novamont S.p.A., Novara (IT)

( * ) Notice: Subject to any disclaimer, the term of this patent is extended or adjusted under 35 U.S.C. 154(b) by 0 days.

(21) Appl. No.: 13/472,976

(22) Filed: May 16, 2012

(65) Prior Publication Data

US 2012/0226060 A1 Sep. 6, 2012

Related U.S. Application Data

(62) Division of application No. 12/599,459, filed as application No. PCT/EP2008/055757 on May 9, 2008, now Pat. No. 8,222,438.

(30) Foreign Application Priority Data

May 10, 2007 (IT) .............................. MI2007A0953

(51) Int. Cl.
*C07C 59/185* (2006.01)
*C09F 7/00* (2006.01)
*C11C 1/00* (2006.01)

(52) U.S. Cl.
USPC ............. 554/121; 554/24; 554/1; 554/132; 554/25; 554/35; 554/134; 560/1

(58) Field of Classification Search
None
See application file for complete search history.

(56) References Cited

U.S. PATENT DOCUMENTS 3,745,033 A * 7/1973 Hutchison ............. 106/270
2004/0034091 A1  2/2004 Castagneto

FOREIGN PATENT DOCUMENTS

| EP | 0 128 484 A1 | 12/1984 |
|---|---|---|
| GB | 348593 A | 5/1931 |
| GB | 604281 A | 7/1948 |
| JP | 2000-204060 A | 7/2000 |
| NL | 6 412 510 A | 5/1965 |
| WO | WO-9212960 A2 | 8/1992 |
| WO | WO-94/10122 A1 | 5/1994 |
| WO | WO-2007/039481 A1 | 4/2007 |

OTHER PUBLICATIONS

Nystrom, R.F. et al., Reductin of organic compounds by lithium aluminum hydrode. II. carboxylic acids, 1947, Journal of the American Chemical Society., 69(10), pp. 2548-2549 (3 pages with ref. pg.).*
Meislichm H, et al., Carboxylic acids and thier derivatives, Ch. 16, 1999, Schaum's outline of Theory and Problems of Organic Chemistry, 3rd Ed., Mcgraw-Hill, (4 pages).*
Adrianov, K. A. et al: "Synthesis of Polyesters and poly(ester-amides) with reticulate molecular structure" Izvestiya Akademii Nauk Sssr, Seriya Khimicheskaya, (1), 158-61 Coden: IASKA6; ISSN:0002-3353, 1967, XP002496185 abstract.
Andrianov, K. A. et al: "Tridinmensional polycondensation of glycerides of dicarboxylic acids with different glycols" Vysokomolekulyarnye Soeineniya, Seriya B: Kratkie Soobshcheniya, 9(6), 431-4 Coden: Vysbai; ISSN: 0507-5483, 1967, XP002496186 abstract.
Andrianov, K. A. et al: "Synthesis and physiochmechanical properties of films based on trifunctional acid esters and epoxy resins" Lakokrasochnye Materialy I IKH Primenenie, (3), 9-10 Coden: Lamaad; ISSN: 0130-9013, 1969, XP002496187 abstract.

* cited by examiner

*Primary Examiner* — Yate K Cutliff
(74) *Attorney, Agent, or Firm* — Novak Druce Connolly Bove + Quigg LLP

(57) ABSTRACT

Process for the production of saturated monocarboxylic acids and triglycerides of saturated carboxylic acids having more than one acid function starting from non-modified vegetable oils containing triglycerides of unsaturated fatty acids, comprising the oxidative cleavage of the unsaturated fatty acids.

14 Claims, No Drawings

TRIGYCERIDES CONTAINING CERTAIN SATURATED CARBOXYLIC ACIDS

CROSS REFERENCE TO RELATED APPLICATIONS

This application is a divisional of application Ser. No. 12/599,459, filed on Nov. 9, 2009 now U.S. Pat. No. 8,222,438, and for which priority is claimed under 35 U.S.C. §120; and this application is the national phase filing of Application No. PCT/EP2008/055757 filed May 9, 2008, which claims priority of Application No. MI2007A000953 filed in Italy on May 10, 2007, under 35U.S.C. §119; the entire contents of all are hereby incorporated by reference.

The present invention relates to a process for the production of saturated monocarboxylic acids and triglycerides of saturated carboxylic acids having more than one acid function starting from non-modified vegetable oils containing triglycerides of unsaturated fatty acids, comprising the oxidative cleavage of the unsaturated fatty acids.

Oxidative cleavage processes starting from unsaturated fatty acids or their derivatives such as, for example, esters of unsaturated fatty acids are known in the literature. They typically comprise a first step (a) in which the olefinic double bond of the unsaturated fatty acid is oxidised to form a vicinal diol, and a second step (b) in which the bond between the two carbon atoms of the vicinal diol moiety is cleaved.

A process of this type is described in EP 0 666 838. In such process the oxidative cleavage is characterised in that both the steps (a) and (b) are performed without any added organic solvent, and in that during step (b) water is added to the reaction product of step (a), thus obtaining a mixture with a water/diol ratio of between 1:1 and 5:1, then reacting the mixture with oxygen, or a compound containing oxygen, in the presence of a cobalt compound as catalyst. This process does not require any purification of the intermediate reaction product (vicinal diol) and does not require the addition of solvents for oxidation of the diol, which is performed in the presence of water. The characteristics of the intermediate product that forms at the end of the first step, in particular its high viscosity, nevertheless make it necessary to add large quantities of water in order to perform the second step of the process. From the point of view of industrial production, this fact is particularly disadvantageous as it involves the need for large-volume reactors. Moreover, the high amount of residual water and the presence of organic residues at the end of the process require a burdensome treatment to recover the dissolved catalyst and dispose of it due to.

A different process for the preparation of saturated carboxylic acids by oxidative cleavage is described in the patent application WO 2007/039481 A1.

According to said application, the oxidative cleavage process is characterised by the use, as starting material, of a derivative—in particular a methyl ester—of a monounsaturated fatty acid. The use of said derivative as starting material produces a less viscous reaction intermediate than the process according to EP 0 666 838, thus making it possible to reduce the amount of water required. The use of said derivative as starting material requires, however, that a reaction of transesterification of the triglycerides contained in the starting vegetable oil is performed upstream the process. The need for said transesterification reaction upstream the oxidative cleavage process has obvious disadvantages of an economic nature. On the one hand the need to use toxic solvents such as methyl alcohol requires appropriate safety measures which significantly affect costs. On the other, the production of glycerol as a by-product of the reaction implies the need to identify outlet markets for the latter. Furthermore, the components present at the end of this process require, for their separation, the use of techniques that exploit their different solubility in water and, for their purification, the use of distillation processes such as, for example, fractional distillation.

A process for the preparation of saturated aliphatic carboxylic acids by oxidative cleavage of unsaturated aliphatic carboxylic acids is described in EP 0 128 484 A1. Said process comprises subjecting unsaturated aliphatic monocarboxylic acid, fatty acid mixtures produced by hydrolyzing vegetable oils, tall oil fatty acids and esters of these fatty acids to a first reaction with peroxides and to a following oxidation by oxygen in the presence of a catalyst comprising at least one heavy metal compound and at least one member selected from the group of a bromine compound and a chlorine compound.

Therefore, the need is felt for a process that avoids the disadvantages of the known processes described above.

With the process according to the present invention, it has been surprisingly discovered that it is possible to produce saturated monocarboxylic acids and triglycerides of saturated carboxylic acids having more than one acid function starting directly from vegetable oils without the need for preliminary modifications such as, for example, transesterifications, of the triglycerides contained in them. The process according to the invention, furthermore, is performed without the need to add large quantities of water, which makes it even more advantageous from the industrial point of view.

The present invention relates to a process for the production of monocarboxylic saturated acids and triglycerides of saturated carboxylic acids having more than one acid function starting from non-modified vegetable oils containing triglycerides of unsaturated fatty acids, characterised by comprising the steps of:

(a) reacting the triglycerides of unsaturated fatty acids with an oxidising compound in the presence of a catalyst for the oxidation reaction of the olefinic double bond of the unsaturated fatty acid, and obtaining a vicinal diol as an intermediate product;

(b) reacting said intermediate product obtained from step (a) with oxygen or a compound containing oxygen, in the presence of a catalyst for the oxidation reaction of the two hydroxyl groups of the vicinal diol to carboxylic groups, and obtaining a reaction product comprising saturated monocarboxylic acids (i) and triglycerides of saturated carboxylic acids having more than one acid function (ii); said step (b) having a water/diol ratio of below 1:1;

(c) separating said saturated monocarboxylic acids (i) from said triglycerides of saturated carboxylic acids having more than one acid function (ii).

According to another aspect of the invention, said step (b) has a water/diol ratio of below 1:3.

According to another aspect of the invention, during step (b) the reaction product is preferably present in form of an aqueous phase and an organic phase.

According to another aspect of the invention, said intermediate product obtained from step (a) is reacted with oxygen or a compound containing oxygen in step (b) without the need for any purification treatment.

According to a further aspect of the invention, said step (b) is carried out without addition of water besides the water in which the catalyst is dissolved.

According to a still further aspect of the invention, both steps (a) and (b) are carried out without the addition of organic solvent.

The starting material for the process according to the present invention is a vegetable oil comprising a mixture of triglycerides of unsaturated fatty acids. Examples of vegetable oils are: soybean oil, olive oil, castor oil, sunflower oil, peanut oil, safflower oil, maize oil, palm oil, jatropha oil, cuphea oil, oils from Brassicaceae such as *Crambe abyssinica, Brassica carinata, Brassica napus* (colza), *Lesquerella*, oils with high monounsaturated acid content etc. The use of sunflower oil and of oils from Brassicaceae is particularly advantageous. The use of sunflower oil with high oleic acid content and of oils from Brassicaceae with high erucic acid content is even more advantageous.

The fatty acid of the triglyceride can be monounsaturated or polyunsaturated. Examples of unsaturated fatty acids are 9-tetradeconoic (myristoleic), 9-hexadecenoic (palmitoleic), 9-octadecenoic (oleic), 12-hydroxy-9-octadecenoic (ricinoleic), 9-cicosenoic (gadoleic), 13-docosenoic (erucic), 15-tetracoscenoic (nervonic), 9,12-octadecadienoic (linoleic), and 9,12,15-octadecatrienoic (linolenic) acid.

Monounsaturated fatty acids are particularly preferred. In the process according to the invention use of oleic acid and of erucic acid is particularly advantageous. In such a case pelargonic acid as saturated monocarboxylic acid is obtained as end product with high yields.

The oxidising compound used to perform step (a) of the process according to the invention is preferably an aqueous solution of hydrogen peroxide in concentrations of between 30 and 70 wt %, preferably between 35 and 60 wt % and even more preferably between 40 and 50 wt %.

The diol resulting from step (a) is made to react—in step (b)—with oxygen or with a compound containing oxygen. The use of air is particularly advantageous and the use of oxygen enriched air is even more advantageous.

Advantageously the catalyst of step (a) belongs to the group consisting of tungsten, molybdenum, and their acids and alkaline salts. The use of tungstic acid or phosphotungstic acid is particularly preferred. Said catalyst is present in quantities of between 0.03% and 3% by moles, preferably between 0.05% and 1.8% by moles and even more preferably between 0.06% and 1.5% by moles with respect to the unsaturated fatty acid.

As regards the catalyst of step (b), it can be added to the reaction mixture as aqueous solution and it belongs advantageously to the class of cobalt and/or manganese based compounds and their mixtures, such as, for example, acetates, chlorides, sulphates, bromides and nitrates, used in quantities of between 0.05% and 3% by moles, preferably between 0.1% and 2% by moles and even more preferably between 0.3% and 1.5% by moles with respect to the diol produced in step (a). The use of cobalt acetate and cobalt chloride is particularly preferred.

Advantageously as inorganic acid can be added to the cobalt-based or cobalt and manganese-based catalyst of step (b). Examples of inorganic acid are phosphoric acid, hydrochloric acid and perchloric acid and their mixtures.

As catalyst of step (b), manganese-based compounds can be advantageously used in a mixture with the cobalt-based compounds. Preferably, said mixtures have a Co:Mn molar ratio comprised between 5:1 and 10:1.

In a preferred form of the process according to the invention, at the beginning of step (a) a small addition of the intermediate that forms at the end of step (a) (so-called reaction activator) is used, as the initial presence of the intermediate that will form promotes activation of the reaction.

The "reaction activator" is added in a quantity ≤5%, preferably ≤3% by weight with respect to the starting oil.

Advantageously, if the reaction activator is not available, it is useful to add to the initial reaction mixture a certain quantity of $H_2O_2$ and wait for the temperature to increase due to the exothermia of the process. When this happens it means that the reaction of the unsaturated fatty acid part of the triglyceride with $H_2O_2$ has occurred and therefore the dihydroxide that activates the reaction has formed.

In a preferred form of the process according to the invention, during step (a) nitrogen is fluxed to distil a part of the water of the process. This prevents excessive dilution of $H_2O_2$. An alternative to nitrogen flow is evaporation under reduced pressure.

In a preferred form of the process according to the invention at the end of step (a) the catalyst is not removed.

The reaction temperature of step (a) and step (b) of the present process is advantageously between 45 and 95° C., preferably between 50 and 90° C.

The reaction temperature of step (a) is advantageously between 55 and 70° C.

The reaction temperature of step (b) is advantageously between 55 and 90° C., more advantageously between 60 and 70° C.

The time necessary for the reaction of step (a) of the present process is between 2 and 10 hours while the time necessary for step (b) is between 3 and 12 hours.

The process according to the invention can be advantageously performed at atmospheric pressure or at low partial oxygen pressures, therefore resulting particularly advantageous in terms of industrial production.

Step (a) is preferably performed at atmospheric pressure.

Step (b) is performed at a pressure greater than atmospheric pressure and preferably ≤20 atm, more preferably ≤15 atm.

When aqueous phase is present, its separation from the organic phase can be performed either at the end of step (a) or at the end of step (b). Advantageously such separation is performed at the end of step (b). The aqueous phase contains the catalyst of step (b), if necessary in a mixture with the catalyst of step (a), which can then be recovered and optionally recycled as catalyst of step (b).

The organic phase is a clear oil consisting of a mixture substantially comprising saturated monocarboxylic acids and triglycerides containing saturated carboxylic acids having more than one acid function, saturated monocarboxylic acids present is the starting mixture and vicinal diol which forms at the end of step (a).

Advantageously the triglycerides can be separated from the saturated monocarboxylic acids by means of distillation processes of the latter. Steam distillation is particularly preferred.

The above mentioned triglycerides containing saturated carboxylic acids having more than one acid function, as such or in chemically modified forms, can be used as intermediates in the production of polymers, surface-active agents, lubricants, lubricant coformulants and drug carriers. Triglycerides containing saturated carboxylic acids having between 1.5 and 2.5 moles of acid groups per mole of triglyceride are preferred.

Said triglycerides containing saturated carboxylic acids can be chemically modified, for example, by means of a reduction reaction where the carboxylic units of the triglyceride containing is converted to hydroxy groups or amine groups. Intermediates containing hydroxyl, amino and other functional groups in the range 1.5-2.5 mole per mole of triglyceride are preferred. Such chemically modified intermediates are obtainable with well known chemical reactions.

Such chemically modified intermediates as well as said triglycerides containing saturated carboxylic acids can be used as monomers for the production of polymers such as: polyesters, polyamides, polyester amides, polyurethanes, polyester-urethanes.

Highly preferred are tryglicerides which contain between 1 and 2.5 moles of azelaic acid, sebacic acid, brassilic acid and their mixtures.

Triglycerides containing the saturated carboxylic acids having more than one acid function can in turn be hydrolysed into glycerol and saturated carboxylic acids. The hydrolysis reaction can be performed through different methods such as hydrolysis with water, hydrolysis with strong acid ion exchange resins and enzyme catalyzed hydrolysis.

The hydrolysis with water, (ratio water/oil comprised between 1:1 and 1:5) is performed at a temperature comprised between 150 and 300° C., preferably between 180 and 270° C., at a pressure equal to the equilibrium pressure of the steam with or without adding hydrolysis catalysts. The hydrolysis is performed at a temperature of 100-120° C. with strong acid ion exchange resins. Examples of such resins are Amberlyst® and Amberlite® type resins (both manufactured by Rohm and Haas Co.).

The enzyme catalyzed hydrolysis is performed with lipases. Said lipases can be advantageously selected from the group comprising: *Candida cylindracea, Candida antartica, Pseudomonas* sp., porcine pancreatic lipase, *Candida rugosa, Geotrichum candidum, Aspergillus niger, Mucor mietei, Rhizopus arrhizus, Rhizopus delemar, Rhizopus niveus, Chromobacterium viscosum, Thermomyces lanugiaosus, Penicillum cyclopium.*

Depending on the type of starting oil, different carboxylic acids can be obtained such as: oxalic acid, malonic acid, succinic acid, glutaric acid, adipic acid, pimelic acid, suberic acid, azelaic acid, sebacic acid, undecandicarboxylic acid, dodecandicarboxylic acid, brassylic acid, tetradecandicarboxylic acid, pentadecandicarboxylic acid.

In a preferred form of the process according to the invention, azelaic acid and brassylic acid are mainly obtained from the hydrolysis reaction, with yields of up to 80% with respect to the quantity of saturated carboxylic acids having more than one acid function theoretically obtainable.

The process according to the invention will now be described with reference to non-limiting examples below.

EXAMPLES

Example 1

Step (a) (Reaction with $H_2O_2$)

The following substances were placed in a reactor:
- 1000 g of sunflower oil with high oleic content (82% oleic acid, 10% linoleic acid, 4.5% palmitic acid, 3.5% stearic acid),
- 5 g tungstic acid (0.7% by moles with respect to the unsaturated fatty acid)
- 50 g of raw hydroxylated oil (intermediate obtained at the end of step (a) coming from a previous reaction, so-called "reaction activator").

The temperature was increased to 60°-65° C. and 280 cc of 49.9% solution of $H_2O_2$ were added in 3 h.

During the reaction nitrogen was fluxed to distil a part of the water of the process and to prevent excessive dilution of $H_2O_2$.

Once the addition of $H_2O_2$ was completed, the reaction was continued at 65° C. for 3 h.

Step (b) (Reaction with Air)

The mixture formed at the end of step (a) was transferred to an autoclave provided with stirring system.

300 g of aqueous solution of 1% cobalt acetate were added (0.4% % by moles with respect to the diol produced in step (a)). The temperature was increased to 70° C. and the reactor was brought to a pressure of 12 atm with air. The air was continuously fluxed to provide a sufficient supply of oxygen. The beginning of the reaction was highlighted by the increase in temperature of the mixture due to the exothermia of the oxidative cleavage. The reaction lasted 8 h.

At the end of step (b) hot separation of the aqueous phase from the organic phase was performed. The aqueous phase contained the catalysts of the first two reaction steps (tungstic acid and cobalt salts), which could be subsequently recovered.

The organic phase (oxidised oil) consisted of triglycerides containing mainly azelaic acid (together with smaller quantities of palmitic acid, stearic acid and dihydroxystearic acid) in a mixture with pelargonic acid and short-chain free monocarboxylic acids.

Step (c)

The organic phase was distilled by steam distillation to separate the light fraction, consisting of 360 g of pelargonic acid and short-chain free monocarboxylic acids.

The distillation residue (790 g) consisted mainly of triglycerides of azelaic acid.

Example 2

The triglycerides remaining in the boiler at the end of the distillation as per example 1 step (c) were subjected to a hydrolysis reaction by adding water in a ratio 1:1 at 180° C. under pressure for 3 h. This reaction released the mono- and dicarboxylic saturated fatty acids from glycerol. Azelaic acid and glycerol were separated from the mixture of fatty acids by means of successive extractions with water at 90° C. By cooling of the aqueous solution, 370 g of azelaic acid were crystallised. The remaining water was passed through a basic ionic exchange resin and then evaporated to recover 100 g of glycerol.

The quantity of azelaic acid obtained, cross-checked by a gas chromatographic analysis, corresponded to a cleavage yield of the oleic acid equal to approximately 70% with respect to the quantity of azelaic acid theoretically obtainable.

The invention claimed is:

1. Triglycerides obtained from vegetable oils containing triglycerides of unsaturated fatty acids by oxidative cleavage of double bonds of unsaturated fatty acids contained in the vegetable oils, said triglycerides containing saturated carboxylic acids having more than one acid function, wherein said saturated carboxylic acids comprise azelaic acid and one or more of glutaric acid, adipic acid, pimelic acid, suberic acid, sebacic acid, undecandicarboxylic acid, dodecandicarboxylic acid, brassylic acid, tetradecandicarboxylic acid, pentadecandicarboxylic acid.

2. Triglycerides according to claim 1 having between 1 and 2.5 moles of acids groups per mole of triglyceride.

3. Triglycerides according to claim 1, wherein the saturated carboxylic acids having more than one acid function are mixtures of azelaic acid, sebacic acid or brassylic acid.

4. Triglycerides according to claim 1, wherein the carboxylic units are chemically modified to hydroxyl or amino group.

5. A method for producing a polymer which comprises polymerizing a triglyceride of saturated carboxylic acids according to claim 1.

6. A lubricating method which comprises applying to a surface to be lubricated a triglyceride of saturated carboxylic acids according to claim 1.

7. A drug carrier composition which comprises a triglyceride of saturated carboxylic acids according to claim 1.

8. Triglycerides according to claim 2, wherein the carboxylic units are chemically modified to hydroxyl or amino group.

9. Triglycerides according to claim 3, wherein the carboxylic units are chemically modified to hydroxyl or amino group.

10. A method for producing a polymer which comprises polymerizing a triglyceride of saturated carboxylic acids according to claim 2.

11. A method for producing a polymer which comprises polymerizing a triglyceride of saturated carboxylic acids according to claim 3.

12. A method for producing a polymer which comprises polymerizing a triglyceride of saturated carboxylic acids according to claim 4.

13. A lubricating method which comprises applying to a surface to be lubricated a triglyceride of saturated carboxylic acids according to claim 2.

14. A drug carrier composition which comprises a triglyceride of saturated carboxylic acids according to claim 2.

* * * * *